United States Patent [19]

Jones et al.

[11] Patent Number: 4,523,049

[45] Date of Patent: Jun. 11, 1985

[54] METHANE CONVERSION PROCESS

[75] Inventors: C. Andrew Jones, Newtown Square; John J. Leonard, Springfield; John A. Sofranko, Malvern; Howard P. Withers, Pottstown, all of Pa.

[73] Assignee: Atlantic Richfield Company, Los Angeles, Calif.

[21] Appl. No.: 600,656

[22] Filed: Apr. 16, 1984

[51] Int. Cl.$^3$ .............................................. C07C 2/00
[52] U.S. Cl. .................................... 585/500; 585/415; 585/417; 585/418; 585/541; 585/654; 585/658; 585/661; 585/943; 585/700
[58] Field of Search ............... 585/500, 541, 700, 415, 585/417, 418, 654, 656, 658, 661, 943

[56] References Cited

U.S. PATENT DOCUMENTS

| 4,205,194 | 5/1980 | Mitchell et al. | 585/500 |
|---|---|---|---|
| 4,239,658 | 12/1980 | Mitchell et al. | 585/500 |
| 4,443,645 | 4/1984 | Jones et al. | 585/500 |
| 4,443,648 | 4/1984 | Jones et al. | 585/500 |

FOREIGN PATENT DOCUMENTS

| 255829 | 5/1926 | United Kingdom | 585/700 |
|---|---|---|---|
| 258608 | 1/1928 | United Kingdom | 585/943 |

OTHER PUBLICATIONS

Keller, G. E., "Synthesis of Ethylene via Oxidative Coupling of Methane," J. of Catalysis, 73, 9–19 (1982).

Primary Examiner—Delbert E. Gantz
Assistant Examiner—Cynthia A. Prezlock
Attorney, Agent, or Firm—Craig E. Larson

[57] ABSTRACT

An improved method for converting methane to higher hydrocarbon products by contacting a hydrocarbon gas comprising methane, an oxygen-containing gas and a reducible metal oxide under synthesis conditions, the improvement which comprises contacting methane and oxygen with a contact solid which also contains a promoting amount of alkali metal, alkaline earth metal, and/or compounds thereof. Sodium is a particularly effective promoter. Stability of the promoted contact agent is enhanced by the presence of minor amounts of phosphorus.

45 Claims, No Drawings

METHANE CONVERSION PROCESS

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of well-head gas, processing facilities usually being located in or near the production fields. Conventional processing of wellhead natural gas yields processed gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. Pat. application Ser. Nos. 522,925 (now U.S. Pat. No. 4,443,649); 522,944 (now U.S. Pat. No. 4,444,984); 522,942 (now U.S. Pat. No. 4,443,648); 522,905 (now U.S. Pat. No. 4,443,645); 522,877 (now U.S. Pat. No. 4,443,647); 522,876 (now U.S. Pat. No. 4,443,644); and 522,906 (now U.S. Pat. No. 4,443,646), all filed Aug. 12, 1983, the entire contents of each being incorporated herein by reference.

Commonly-assigned U.S. patent application Ser. No. 522,935, filed Aug. 12, 1983, discloses and claims a process which comprises contacting methane with an oxidative synthesizing agent under elevated pressure (e.g., 2-100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. patent application Ser. No. 522,937, filed Aug. 12, 1983, discloses and claims a process for the conversion of methane to higher hydrocarbons which comprises contacting methane with an oxidative synthesizing agent containing a promoting amount of alkali metal and/or compounds thereof. The entire content of this application is incorporated herein by reference.

Commonly-assigned U.S. patent application Ser. No. 522,936, filed Aug. 12, 1983, discloses and claims a process for the conversion of methane to higher hydrocarbons which comprises contacting methane with an oxidative synthesizing agent containing a promoting amount of alkaline earth metal and/or compounds thereof. The entire content of this application is incorporated herein by reference.

Commonly-assigned U.S. patent application Ser. No. 06/600,665 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof. The entire content of this application is incorporated herein by reference.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

Commonly-assigned U.S. patent application Ser. No. 06/600,917 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof. The entire content of this application is incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. patent application Ser. No. 06/600,669 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. The entire content of this application is incorporated herein by reference.

In a typical application of the foregoing processes for the oxidative conversion of methane, methane feed is contacted with a reducible metal oxide and regeneration is accomplished separately by contacting the reduced metal oxide with an oxygen-containing gas (e.g., air). Thus, a cyclic redox process results in which methane reaction and reoxidation of the metal oxide "reagent" are performed separately and repeatedly for a continuous process.

Such a procedure presents several disadvantages for large scale continuous operation. One disadvantage is the large quantity of solid cycling between methane reaction and reoxidation in such a way that the methane and oxygen are not mixed. Another disadvantage is the necessity of developing a composition that is resistant to mechanical attrition and repeated exposure to reductive and oxidative environments.

Hinsen and Baerns recently reported studies of a continuous mode for the oxidative coupling of methane wherein regenerating air is cofed with the methane feed. Hinsen, W. and Bearns, M., "Oxidative Kopplung von Methan zu $C_2$-Kohlenwasserstoffen in Gegenwart unterschiedlicher Katalysatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600°–750° C., they report results of approximately 53% selectively to ethane and ethylene at 8% methane conversion for a feed consisting of about 50% methane, 25% air and 25% nitrogen. Other metal oxides studied by Hinsen and Baerns included oxides of Bi, Sb, Sn and Mn.

SUMMARY OF THE INVENTION

It has now been found that the conversion of methane to higher hydrocarbons in the presence of oxygen is improved by contacting a first, hydrocarbon gas comprising methane and a second, oxygen-containing gas with a promoted contact solid which comprises: (a) at least one reducible oxide of at least one metal which oxide(s) when contacted with methane at methane conversion conditions (preferrably at a temperature within the range of about 500° to 1000° C.) are reduced and produce higher hydrocarbon products and water and (b) a promoting amount of at least one promoter selected from the group consisting of alkali metals, alkaline earth metals, and compounds thereof. Preferred reducible oxides include oxides of metals selected from the group consisting of Mn, Sn, In, Ge, Pb, Sb and Bi. Preferred reducible oxides also include oxides of metals selected from the group consisting of Pr, Tb and Ce. More preferably, reducible oxides are oxides of Mn, Pr and/or Tb. Reducible oxides of Mn are, currently, particularly preferred. Alkali metals are selected from the group consisting of Li, Na, K, Rb and Cs. Alkaline earth metals are selected from the group consisting of Mg, Ca, Sr, and Ba. A currently preferred alkaline earth metal is Ca. However, alkali metals are preferred promoters. More preferred promoters are lithium and sodium. Sodium is a particularly preferred promoter.

The stability of the promoted contact solid is further enhanced by incorporating a stabilizing amount of phosphorus into the composition.

The improved process of the present invention produces higher methane conversion at similar hydrocarbon selectivity or increased hydrocarbon selectivity at similar methane conversion, as compared to prior methods such as that taught by Hinsen and Baerns, supra.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The oxygen-containing gas generally comprises molecular oxygen: other gases such as nitrogen and carbon oxides may be present. A preferred oxygen-containing gas is air.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. It is preferred to maintain the volume ratio of hydrocarbon/oxygen within the range of about 0.1–100:1, more preferably within the range of about 1–50:1. Methane/air feed mixtures containing about 50 to 90 volume % methane have been found to comprise a desirable feedstream. Further dilution of the feedstream with gases such as nitrogen are not necessary.

The contact solid which is contacted with methane in the first stage of the present process has heretofore been generally referred to as a promoted oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof.

Reducible oxides of cerium, praseodymium, and terbium have also been found to be effective for the conversion of methane to higher hydrocarbons when the rare earth component is associated with an alkali metal component (i.e., lithium, sodium, potassium, rubidium, cesium and compounds thereof) and/or an alkaline earth metal component (i.e., magnesium, calcium, strontium, barium, and compounds thereof).

The contact solid employed in the process of the present invention contains, in addition to the reducible metal oxide component, at least one alkali or alkaline earth metal. The atomic ratio in which these materials are combined to form the contact solid is not narrowly critical. However, the preferred atomic ratio of the reducible oxide component (expressed as the metal, e.g., Mn) to the alkali/alkaline earth metal component (expressed as the metal, e.g., Na) is within the range of about 0.1-100:1, more preferably within the range of about 0.3-10:1.

The contact solid may optionally contain at least one phosphorus component. The amount of phosphorus contained in the contact solid is again not narrowly critical. The atomic ratio of phosphorus to the reducible oxide component (expressed as the metal, e.g., Mn) is preferably less than about 2:1. More preferably, this ratio is within the range of about 0.1-0.5:1.

A preferred contact solid used in the process of this invention may be further expressed by the following empirical formula:

$$A_a B_b P_c O_d$$

wherein A is selected from the group consisting of Mn, Sn, In, Ge, Pb, Sb, Bi, Pr, Tb, Ce and mixtures thereof; B is selected from the group consisting of alkali and alkaline earth metals including mixtures thereof; a to d indicate the atomic ratio of each component; and when a is 10, b is within the range of about 1-33, c is within the range of about 0-20, and d has a value which is determined by the valence and proportions of the other elements present.

The metal components may be associated with support materials such as silica, alumina, titania, magnesia, zirconia and the like and combination thereof. When employing agents containing rare earth components—oxides of Ce, Pr, and Tb—the rare earth oxides preferably serve as supports.

Reducible oxides of manganese have been found to be particularly desirable for methane conversion according to the method of the present invention when associated with an alkali metal (preferably sodium). Particularly preferred agents comprise silica- and/or magnesia-supported solids containing oxides of manganese and sodium.

The solid contacted with methane and an oxygen-containing gas can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkaline metal or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300 to 1200° C. Particular calcination temperatures will vary depending upon the particular metal compound or compounds employed.

Regardless of how the components of the agent are combined, the composite will be dried and calcined at elevated temperatures prior to use of the process of this invention.

Preferably, methane and oxygen are contacted with the agent in the substantial absence of catalytically effective nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 300° to 1200° C., more preferably within the range of about 500° to 1000° C. Best results for contact solids containing manganese have been found at operating temperatures within the range of about 800° to 900° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 hr.$^{-1}$, more preferably within the range of about 600 to 40,000 hr.$^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the oxygen cofed with methane to the contact zone.

The contact solids may be maintained in the contact zone as fixed, moving, or fluidized beds of solids. A fixed bed of solids is currently preferred for the method of this invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following examples.

EXAMPLE 1

A contact solid consisting of 10 wt. % Mn/5 wt. % $Na_4P_2O_7$ on silica was prepared by impregnating the silica support with appropriate amounts of sodium pyrophosphate and manganese (as manganese acetate). The impregnated solid was dried for 2 hours at 110° C. and then calcined in air for 16 hours at 850° C. A quartz tube reactor (12 mm. inside diameter) was charged with 10 ml. of the calcined solids and the reactor was heated to 700° C. with a heated stream of nitrogen. Results obtained when methane/air mixtures were contacted with the calcined solid are shown below in Table 1. Also shown in Table 1 are results obtained when methane and air were cyclically introduced to the reactor.

The first three runs shown in Table 1 used a cyclic process in which methane was passed over the solid for 2 minutes followed by a 10 minute $N_2$ purge, a 20 minute air reoxidation, a 15 minute $N_2$ purge, and then repeating the cycle. Also see Run 8. Runs 4–7, 9 and 10 used a mixed feed containing 90 vol. % methane and 10 vol. % air. Runs 11–15 used a mixed feed containing 50 vol. % methane and 50 vol. % air. The total gas hourly space velocity (GHSV) of all of the runs shown in Table I was 600 hr.$^{-1}$. The experimental results presented in Table 1 include methane conversions and product selectivities calculated on a molar basis. Results are based on gas chromatographic analysis of total reactor effluent collected over the run time. Changes in feed composition for the methane/air runs and changes in flow rate and temperature were accomplished by diverting the feed stream from the reactor for a short period of time to adjust the operating variable and then reintroducing the feed to the reactor at the various operating conditions shown in Table 1.

TABLE 1

Methane/Air Mixtures Over 10% Mn/5% $Na_4P_2O_7$/Silica (total GHSV = 600 hr.$^{-1}$)

| Run No. (time in min) | Feed (%) | Rxn Temp. | $CH_4$ % Conv. | % Selectivity to: | | | |
|---|---|---|---|---|---|---|---|
| | | | | $C_2+$ | CO | $CO_2$ | Coke |
| 1(2) | $CH_4$ | 700° C. | 4.4 | 59.0 | 15.9 | 20.4 | 4.5 |
| 2(2) | $CH_4$ | 800 | 12.0 | 61.7 | 5.0 | 29.1 | 4.1 |
| 3(2) | $CH_4$ | 800 | 13.9 | 68.3 | 5.7 | 23.0 | 2.9 |
| 4(10) | $CH_4$(90), AIR(10) | 600 | 1.5 | 6.7 | — | 93.3 | — |
| 5(10) | $CH_4$(90), AIR(10) | 700 | 3.0 | 53.0 | — | 47.0 | — |
| 6(10) | $CH_4$(90), AIR(10) | 750 | 5.6 | 66.0 | 7.1 | 26.8 | — |
| 7(10) | $CH_4$(90), AIR(10) | 800 | 6.9 | 70.3 | 7.2 | 22.4 | — |
| 8(30) | $CH_4$ | 800 | 1.6 | 89.8 | — | 10.2 | — |
| 9(30) | $CH_4$(90), AIR(10) | 800 | 4.4 | 68.3 | 9.0 | 22.6 | — |
| 10(60) | $CH_4$(90), AIR(10) | 800 | 3.9 | 67.7 | 10.3 | 21.9 | — |
| 11(30) | $CH_4$(50) | 600 | 5.6 | — | — | 100 | — |

TABLE 1-continued

Methane/Air Mixtures Over 10% Mn/5% $Na_4P_2O_7$/Silica (total GHSV = 600 hr.$^{-1}$)

| Run No. (time in min) | Feed (%) | Rxn Temp. | $CH_4$ % Conv. | % Selectivity to: | | | |
|---|---|---|---|---|---|---|---|
| | | | | $C_2+$ | CO | $CO_2$ | Coke |
| 12(30) | AIR(50) $CH_4$(50) AIR(50) | 700 | 15.3 | 15.1 | 5.9 | 78.9 | — |
| 13(30) | $CH_4$(50), AIR(50) | 750 | 20.1 | 35.8 | 6.3 | 57.8 | — |
| 14(30) | $CH_4$(50), AIR(50) | 800 | 22.6 | 46.9 | 7.9 | 45.1 | — |
| 15(60) | $CH_4$(50) AIR(50) | 850 | 22.8 | 49.6 | 12.2 | 38.1 | — |

Run 7 demonstrates that improved hydrocarbon selectivity can be obtained using the method of this invention at conversion levels similar to those reported by Hinsen and Baerns. Run 15 demonstrates that substantial increases in methane conversion can be realized while maintaining hydrocarbon selectivities comparable to those reported by Hinsen and Baerns. The data also demonstrates that use of higher operating temperatures offers improved process results.

EXAMPLE 2

This example was carried out in the same manner as Example 1 using the same contact solid and shows the effect of increasing space velocity on conversion and selectivity. A 50% methane, 50% air feed mixture was studied at 800° C. and various total feed flow rates. The results are shown in Table 2. Runs 1–7 indicate that as the space velocity is increased there is little or no change in methane conversion with a maximum in hydrocarbon selectivity at a gas hourly space velocity (GHSV) of 2400 hr.$^{-1}$. As the GHSV is increased above 9600 both conversion and selectivity decrease. Table 2 also includes data for % $O_2$ conversion and methane weight hourly space velocity ($CH_4$ WHSV: weight of methane fed per hour per weight of contact solid in the reactor).

TABLE 2

1:1, Methane Air Mixtures Over 10% Mn, 5% $Na_4P_2O_7$ on Silica at 800° C.

| Run No. (time in min) | Total GHSV (hr$^{-1}$) | $CH_4$ WHSV (hr$^{-1}$) | % $CH_4$ Conv. | % Selectivity to: | | | % $O_2$ Conver. |
|---|---|---|---|---|---|---|---|
| | | | | $C_2+$ | CO | $CO_2$ | |
| 1(30) | 600 | 0.38 | 22.6 | 47 | 8 | 45 | 93 |
| 2(30) | 800 | 0.51 | 22.7 | 49 | 9 | 42 | 87 |
| 3(30) | 1000 | 0.64 | 22.7 | 51 | 9 | 40 | 85 |
| 4(30) | 1200 | 0.76 | 22.4 | 52 | 10 | 38 | 85 |
| 5(30) | 2400 | 1.53 | 24.1 | 57 | 10 | 33 | 87 |
| 6(30) | 4800 | 2.92 | 23.2 | 55 | 11 | 34 | 85 |
| 7(30) | 9600 | 5.78 | 22.4 | 55 | 11 | 34 | 84 |
| 8(15) | 28800 | 17.53 | 10.4 | 48 | 13 | 39 | 42 |
| 9(15) | 38400 | 23.03 | 7.0 | 45 | 14 | 40 | 27 |

EXAMPLE 3

A series of experiments similar to Examples 1 and 2 showed that by changing the composition of the contact solid to 15 wt. % Mn/4 wt. % $Na_4P_2O_7$ on silica, further improvements in methane conversion and hydrocarbon selectivity could be obtained. This example also shows that as the percentage of air in the feed is increased for a given set of conditions, the methane conversion increases and the hydrocarbon selectivity decreases. Table 3 summarized the results for this example. By comparing run 6 in Table 2 with run 12 in Table 3 one can see the improvement in using 15 wt. % Mn/4 wt. % $Na_4P_2O_7$ on silica as the contact solid.

TABLE 3

Methane/Air Mixtures Over 15% Mn, 4% $Na_4P_2O_7$ on Silica

| Run No. (time in min) | Total GHSV ($hr^{-1}$) | $CH_4$ WHSV ($hr^{-1}$) | Feed (%) | % $CH_4$ Conv. | Temp °C. | % Selectivity to: $C_2+$ | CO | $CO_2$ |
|---|---|---|---|---|---|---|---|---|
| 1(4)* | 600 | 0.70 | $CH_4$(100) | 6.9 | 700 | 65.4 | — | 28.8 |
| 2(4) | 600 | 0.70 | $CH_4$(100) | 17 | 800 | 56.6 | 7.1 | 35.0 |
| 3(30) | 1200 | 1.26 | $CH_4$(90), AIR(10) | 2.8 | 700 | 56.0 | — | 44.0 |
| 4(30) | 1200 | 1.26 | $CH_4$(90), AIR(10) | 2.5 | 750 | 48.0 | — | 52.0 |
| 5(30) | 1200 | 1.26 | $CH_4$(90), AIR(10) | 3.2 | 800 | 65.3 | 9.4 | 25.2 |
| 6(30) | 1200 | 1.26 | $CH_4$(90), AIR(10) | 4.7 | 800 | 67.2 | 8.5 | 24.3 |
| 7(30) | 1200 | 1.12 | $CH_4$(80), AIR(20) | 6.7 | 800 | 64.3 | 7.4 | 28.2 |
| 8(30) | 1200 | 0.98 | $CH_4$(70), AIR(30) | 11 | 800 | 60.5 | 8.1 | 31.3 |
| 9(30) | 1200 | 0.98 | $CH_4$(70), AIR(30) | 12 | 850 | 66.6 | 10.1 | 23.2 |
| 10(30) | 2400 | 1.96 | $CH_4$(70), AIR(30) | 13 | 850 | 69.1 | 10.3 | 20.6 |
| 11(30) | 2400 | 2.24 | $CH_4$(80) AIR(20) | 8.3 | 850 | 74.5 | 9.1 | 16.5 |
| 12(30) | 4800 | 2.81 | $CH_4$(50), AIR(50) | 25 | 800 | 60.0 | 11.1 | 28.8 |
| 13(30) | 2400 | 1.4 | $CH_4$(50), AIR(50) | 24 | 800 | 56.0 | 10.0 | 34.0 |
| 14(4) | 1200 | 1.4 | $CH_4$(100), | 9.8 | 800 | 81.3 | 6.5 | 12.3 |

*Coke selectivity was 5.8% for this inital run.

EXAMPLE 4

Feeds containing more than 50% air were studied in this example which used a contact solid consisting of 15 wt. % Mn/4wt. % $Na_4P_2O_7$ on silica. Feeds containing 70, 75 and 80% air were studied at temperatures of 600° to 800° C. and a constant total gas hourly space velocity (GHSV) of 2400 $hr.^{-1}$. Large exotherms were observed. The results, shown in Table 4, show that large amounts of air in the feed (greater than 50%) produced relatively inferior hydrocarbon selectivities. The duration of each run shown was 30 minutes.

TABLE 4

| Run No. | Temp. % | $CH_4$ WHSV ($hr^{-1}$) | Feed (%) | % $O_2$ Conv. | % $CH_4$ Conv. | % Selectivity to: $C_2+$ | CO | $CO_2$ |
|---|---|---|---|---|---|---|---|---|
| 1 | 600 | 0.41 | $CH_4$(30) AIR(70) | 7 | 3.2 | 0 | 0 | 100 |
| 2 | 700 | 0.41 | $CH_4$(30) AIR(70) | 49 | 19 | 1.2 | 4.4 | 94.4 |
| 3 | 800 | 0.41 | $CH_4$(30) AIR(70) | 93 | 34 | 19.2 | 3.1 | 77.7 |
| 4 | 700[a] | 0.41 | $CH_4$(30) AIR(70) | 60 | 22 | 3.5 | 4.2 | 92.4 |
| 5 | 800[a] | 0.41 | $CH_4$(30) AIR(70) | 92 | 39 | 34.1 | 6.4 | 59.6 |
| 6 | 800[a] | 0.34 | $CH_4$(25) AIR(75) | 93 | 47 | 30.7 | 6.0 | 63.3 |
| 7 | 880[b] | 0.34 | $CH_4$(25) AIR(75) | 93 | 48 | 32.8 | 7.8 | 59.5 |
| 8 | 800[a] | 0.27 | $CH_4$(20) AIR(80) | 93 | 56 | 27.3 | 5.5 | 67.2 |

[a] The temperature shown is the initial reaction temperature. The subsequent axotherm was allowed to occur in these runs without the temperature controller responding.
[b] The temperature shown is the initial reaction temperature. The temperature controller responded during the run to maintain reaction temperatures close to the initial temperature shown.

port with appropriate amounts of sodium (as sodium acetate) and tin (provided as 7% solution of tin tartrate in hydrochloric acid). The impregnated solid was dried

EXAMPLE 5

A contact solid consisting of 10 wt. % Sn/2 wt. % Na on silica was prepared by impregnating the silica support by impregnating the silica support for 2 hours at 110° C. and then calcined in air for 16 hours at 850° C. Using the procedure described above in Example 1, a number of methane/air runs were performed over this solid at varying feed compositions operating temperatures and space velocities. Results are shown below in Table 5. The duration of each run shown was 30 minutes.

TABLE 5

$CH_4$/Air Mixtures Over 10% Sn/2% Na on Silica

| Run No. | Feed (%) | Rxn Temp. | Total GHSV | $CH_4$ % Conv. | % Selectivity to: $C_2+$ | CO | $CO_2$ |
|---|---|---|---|---|---|---|---|
| 1 | $CH_4$(90) AIR(10) | 600° C. | 1200 $hr^{-1}$ | 0.1 | 0 | 0 | 100 |
| 2 | $CH_4$(90) | 700 | 1200 | 2.9 | 76.9 | 17.0 | 6.1 |

TABLE 5-continued

CH$_4$/Air Mixtures Over 10% Sn/2% Na on Silica

| Run No. | Feed (%) | Rxn Temp. | Total GHSV | CH$_4$ % Conv. | % Selectivity to: C$_2$+ | CO | CO$_2$ |
|---|---|---|---|---|---|---|---|
| 3 | CH$_4$(90) AIR(10) | 800 | 1200 | 3.0 | 51.8 | 22.6 | 25.6 |
| 4 | CH$_4$(80) AIR(20) | 800 | 1200 | 4.7 | 37.8 | 18.6 | 44.0 |
| 5 | CH$_4$(70) AIR(30) | 800 | 1200 | 7.8 | 32.0 | 12.4 | 55.7 |
| 6 | CH$^4$(60), AIR(40) | 800 | 1200 | 10.6 | 28.8 | 10.6 | 60.5 |
| 7 | CH$_4$(80) AIR(20) | 800 | 2400 | 4.4 | 39.4 | 13.8 | 46.9 |

EXAMPLE 6

A contact solid consisting of 50 wt. % Mn on silica was prepared by impregnating the silica support with appropriate amounts of manganese (provided as a solution of manganese acetate). The impregnated solid was dried for 2 hours at 110° C. and then calcined in air for 16 hours at 850° C. Using the procedure described above in Example 1, a number of methane/air runs were performed over this solid at varying feed compositions operating temperatures and space velocities. Results are shown below in Table 6. The duration of each run shown was 30 minutes.

TABLE 6

CH$_4$/Air Mixtures Over 50% Mn on Silica

| Run No. | Feed (%) | Rxn Temp. | Total GHSV | CH$_4$ % Conv. | % Selectivity to: C$_2$+ | CO | CO$_2$ |
|---|---|---|---|---|---|---|---|
| 1 | CH$_4$(45) AIR(55) | 750° C. | 1800 hr$^{-1}$ | 17.1 | 7.98 | 14.5 | 77.4 |
| 2 | CH$_4$(70) AIR(30) | 750 | 1800 | 7.9 | 15.35 | 30.2 | 54.4 |
| 3 | CH$_4$(70) AIR(30) | 750 | 3600 | 7.55 | 14.44 | 28.3 | 57.2 |
| 4 | CH$_4$(70) AIR(30) | 750 | 5400 | 7.75 | 16.76 | 29.2 | 53.8 |

EXAMPLE 7

A contact solid consisting of 5 wt. % Mn on silica was prepared by impregnating the silica support with appropriate amounts of an aqueous solution of manganese acetate. The impregnated solid was dried for 2 hours at 110° C. and then calcined in air for 16 hours at 850° C. Using the procedure described above in Example 1, a number of methane/air runs were performed over this solid at varying feed compositions operating temperatures and space velocities. Results are shown below in Table 7. The duration of each run shown was 30 minutes.

TABLE 7

CH$_4$/Air Mixtures Over 5% Mn on Silica

| Run No. | Feed (%) | Rxn Temp. | Total GHSV | CH$_4$ % Conv. | % Selectivity to: C$_2$+ | CO | CO$_2$ |
|---|---|---|---|---|---|---|---|
| 1 | CH$_4$(95.2) AIR(4.8) | 650° C. | 600 hr$^{-1}$ | 1.13 | 2.54 | 44.9 | 52.4 |
| 2 | CH$_4$(95.2) AIR(4.8) | 700 | 600 | 1.23 | 4.28 | 52.8 | 42.8 |
| 3 | CH$_4$(95.2) AIR(4.8) | 750 | 600 | 1.22 | 7.9 | 50.0 | 42.1 |
| 4 | CH$_4$(95.2) AIR(4.8) | 800 | 600 | 1.32 | 15.4 | 51.5 | 32.0 |

What is claimed is:

1. In an improved method for converting methane to higher hydrocarbon products which comprises contacting a gas comprising methane with a contact solid comprising at least one reducible oxide of at least one metal which oxide when contacted with methane at a temperature within the range of about 500° to 1000° C. is reduced and produces higher hydrocarbon products and water, the improvement which comprises conducting the contacting in the presence of an oxygen-containing gas, said solid further comprising at least one member selected from the group consisting of alkali metals, alkaline earth metals, and compounds thereof.

2. The method of claim 1 wherein said hydrocarbon gas and said oxygen-containing gas are contacted with said solid at a temperature selected within the range of about 300° to 1200° C.

3. The method of claim 1 wherein said hydrocarbon gas and said oxygen-containing gas are contacted with said solid at a temperature selected within the range of about 500° to 1000° C.

4. The method of claim 1 wherein the contact solid is described by the empirical formula:

$$A_a B_b P_c O_d$$

wherein A is selected from the group consisting of Mn, Sn, In, Ge, Pb, Sb, Bi, Pr, Tb, Ce and mixtures thereof; B is selected from the group consisting of Li, Na, K, Rb, Cs, Mg, Ca, Sr, Ba and mixtures thereof; a, b, c and d indicate the atomic ratio of earth component; and when a is 10, 6 is within the range of about 1–33, c is within the range of about 0–20, and d has a value which is determined by the valence and proportion of the other elements present.

5. A method for converting methane to higher hydrocarbon products which comprises contacting hydrocarbon gas comprising methane and an oxygen-containing gas at a temperature within the range of about 300° to 1200° C. with a contact solid to produce higher hydrocarbon products and water, which solid comprises:
   (a) at least one reducible oxide of at least one metal selected from the group consisting of Mn, Sn, In, Ge, Pb, Sb and Bi and
   (b) at least one promoter selected from the group consisting of alkali metals, alkaline earth metals, and compounds thereof.

6. The method of claim 5 wherein the hydrocarbon gas comprising methane contains from about 40 to about 100 volume percent methane.

7. The method of claim 5 wherein the gas comprising methane contains from about 80 to about 100 volume percent methane.

8. The method of claim 5 wherein the gas comprising methane contains from about 90 to about 100 volume percent methane.

9. The method of claim 5 wherein the gas comprising methane is derived from natural gas.

10. The method of claim 5 wherein the gas comprising methane is derived from processed natural gas.

11. The method of claim 5 wherein the oxygen-containing gas is air.

12. The method of claim 5 wherein said hydrocarbon gas and said oxygen-containing gas are contacted with said solid at a temperature within the range of about 500° to 1000° C.

13. The method of claim 5 wherein the volume ratio of hydrocarbon to oxygen is within the range of about 0.1–100:1.

14. The method of claim 5 wherein the volume ratio of hydrocarbon to oxygen is within the range of about 1–50:1.

15. The method of claim 5 wherein said solid comprises at least one member of the group consisting of alkali metals and compounds thereof.

16. The method of claim 15 wherein the alkali component is selected from the group consisting of sodium, sodium compounds and mixtures thereof.

17. The method of claim 15 wherein the alkali metal component is selected from the group consisting of potassium, potassium compounds and mixtures thereof.

18. The method of claim 15 wherein the alkali metal component is selected from the group consisting of lithium, lithium compounds and mixtures thereof.

19. The method of claim 5 wherein the said reducible oxide and the said promoter are associated with a support material.

20. The method of claim 19 wherein the support material is silica.

21. The method of claim 5 wherein the contact solid further comprises at least one member selected from the group consisting of phosphorus.

22. The method of claim 5 wherein said reducible oxide comprises a reducible oxide of manganese.

23. The method of claim 22 wherein said solid comprises at least one member of the group consisting of Na, Li, and compounds thereof.

24. The method of claim 23 wherein said contacting is carried out at a temperature within the range of about 800° to 900° C.

25. A method for converting methane to higher hydrocarbon products which comprises contacting a hydrocarbon gas comprising methane and an oxygen-containing gas at a temperature within the range of about 300° to 1200° C. with a contact solid to produce higher hydrocarbon products and water, which solid comprises:
   (a) at least one reducible oxide of at least one metal selected from the group consisting of Pr, Tb and Ce and
   (b) at least one member of the group consisting of alkali metals, alkaline earth metals, and compounds thereof.

26. The method of claim 25 wherein the hydrocarbon gas comprising methane contains from about 40 to about 100 volume percent methane.

27. The method of claim 25 wherein the hydrocarbon gas comprising methane contains from about 80 to about 100 volume percent methane.

28. The method of claim 25 wherein the hydrocarbon gas comprising methane contains from about 90 to about 100 volume percent methane.

29. The method of claim 25 wherein the gas comprising methane is derived from natural gas.

30. The method of claim 25 wherein the gas comprising methane is derived from processed natural gas.

31. The method of claim 25 wherein the oxygen-containing gas is air.

32. The method of claim 25 wherein said hydrocarbon gas and said oxygen-containing gas are contacted with said solid at a temperature within the range of about 500° to 1000° C.

33. The method of claim 25 wherein the volume ratio of hydrocarbon in said hydrocarbon gas to oxygen in said oxygen-containing gas is within the range of about 0.1–100:1.

34. The method of claim 25 wherein the volume ratio of hydrocarbon in said hydrocarbon gas to oxygen in said oxygen-containing gas is within the range of about 1–50:1.

35. The method of claim 25 wherein said solid comprises at least one member of the group consisting of alkali metals and compounds thereof.

36. The method of claim 35 wherein said reducible oxide comprises a reducible oxide of Pr.

37. The method of claim 36 wherein said reducible oxide of Pr is provided as a support for at least one of the other components of said solid.

38. The method of claim 36 wherein said solid comprises at least one member of the group consisting of Na, Li, and compounds thereof.

39. The method of claim 35 wherein said reducible oxide comprises a reducible oxide of Tb.

40. The method of claim 39 wherein said reducible oxide of Tb is provided as a support for at least one of the other components of said solid.

41. The method of claim 39 wherein said solid comprises at least one member of the group consisting of Na, Li, and compounds thereof.

42. The method of claim 35 wherein said reducible oxide comprises a reducible oxide of Ce.

43. The method of claim 42 wherein said solid further comprises at least one reducible oxide of at least one metal selected from the group of Mn, Sn, In, Ge, Pb, Sb and Bi.

44. The method of claim 43 wherein said solid comprises a reducible oxide of Mn.

45. The method of claim 43 wherein said reducible oxide of Ce is provided as a support for at least one of the alkali metal components of said solid.

* * * * *